United States Patent [19]

Prodi

[11] Patent Number: 4,704,528

[45] Date of Patent: Nov. 3, 1987

[54] DEVICE FOR THE SEPARATION OF AIRBORNE PARTICLES INTO CLASSES BY GRAIN SIZE

[76] Inventor: Vittorio Prodi, Via Martinelli, 7, 40137 Bologna, Italy

[21] Appl. No.: 732,742

[22] Filed: Apr. 16, 1985

[30] Foreign Application Priority Data

Apr. 19, 1984 [IT] Italy .................. 3432 A/84

[51] Int. Cl.⁴ ............................. G01N 23/08
[52] U.S. Cl. .................... 250/308; 250/304; 250/435
[58] Field of Search .......... 250/308, 304, 435; 73/432 PS, 863.23

[56] References Cited

U.S. PATENT DOCUMENTS

| | | | |
|---|---|---|---|
| 3,854,321 | 12/1974 | Dahneke | 73/432 PS |
| 3,952,207 | 4/1976 | Leschonski et al. | 73/432 PS |
| 4,213,852 | 7/1980 | Etkin | 73/432 PS |
| 4,298,836 | 11/1981 | Groves et al. | 73/432 PS |
| 4,606,232 | 8/1986 | Prodi | 73/863.23 |

Primary Examiner—Carolyn E. Fields
Assistant Examiner—Richard E. Hanig
Attorney, Agent, or Firm—Omri M. Behr

[57] ABSTRACT

A device of improved type for the separation of airborne particles by grain size is described.

The principle characteristic of the present invention lies in the fact that it comprises: a first base body in which is formed a first cavity on the edge of which rests a plate on which is deposited a filter; two second bodies, one inside the other, in such a way as to define between them an annular channel in which is ducted filtered air and communicating with the said first cavity through a second cylindrical cavity defined by the lower surface of a base wall of the said inner second body and the upper surface of the said filter; and an annular nozzle located in the said channel and operable to eject into it a quantity of particle-bearing air in such a way that the particles of dust present in this are deposited on the said filter.

13 Claims, 2 Drawing Figures

U.S. Patent  Nov. 3, 1987  4,704,528

DEVICE FOR THE SEPARATION OF AIRBORNE PARTICLES INTO CLASSES BY GRAIN SIZE

BACKGROUND OF THE INVENTION

Figure 2:
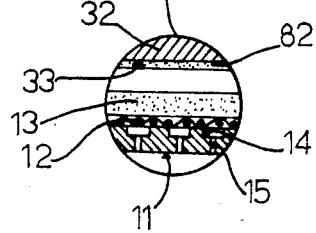

The present invention relates to a device of improved type for the separation of airborne particles such as an aerosol, into grain size classes. Such a device is an instrument which permits the deposition onto a filter of dust particles on which it is then possible to perform a series of chemical and physico-chemical analyses in dependence on the dimensions thereof, for the purpose of determining the risk from inhalation of dust present in a predetermined environment. The said device is utilised in the testing of industrial and environmental health in medical physics and in powder technology generally.

Devices currently in commercial use consist schematically of an L-shaped channel of rectangular outline through which filtered air is passed. This channel thus has two parts the first of which is defined by a first nozzle which ejects filtered air into the second part which is delimited above by a body and below by a support plate on which a filter is positioned. Within the first nozzle there is located a second nozzle which ejects the particle-bearing air or aerosol into a zone of the first part of the channel itself. In this way those particles of dust which have the same dimensions tend to be disposed within the same band of fluid flow which passes out downstream of the said curvature; it is thus possible to think of the fluid as a plurality of bands each of which includes the particles of a single grain size class. The successive bands are deposited on the filter starting from the band with the particles of greater diameter. Experimentally it is noted that the particles of smaller diameter are not clearly separated from one another and that these are deposited together in the portions of the filter spaced furthest from the curvature.

The devices described above have various disadvantages.

In particular, they have a low sampling capacity for the purpose of being utilised in testing environmental health. Moreover, if a diagram is constructed on the abscissa of which is plotted the distance of deposition of the particles from the curvature of the channel, and on the ordinate of which is plotted the aerodynamic diameter of the particles, there is obtained a curve which is linear in the first part relating to the particles of greater diameter, and which is nonlinear and very steep in the second part, relating to the particles of smaller diameter, which may be, however, those of greatest interest in the testing of environmental hygiene, that is to say for determining the toxicity of certain inhalations. This non-linearity of the curve of the diagram for the particles of smaller diameter is caused by the fact that the devices currently used do not succeed in separating completely the particles of such grain size classes from one another, with the consequence that, in a certain range of diametral dimensions; the particles are deposited on the same portion of the filter. In conclusion, the orthogonal projection of the aerosol stream onto the plane of the filter permits a distinct separation only between the bands with particles having a larger diameter.

SUMMARY OF THE INVENTION

The object of the present invention is that of providing a device of improved type for the separation of airborne particles into grain size classes, which will be free from the said disadvantages and which, that is to say, will permit the separation of even particles of smaller diameter into different grain size classes thereby allowing a linearisation of the curve of the first mentioned diagram to be obtained even for that portion of the curve relating to the particles of smaller diameter.

Further objects and advantages will become apparent in the description which follows.

According to the present invention there is provided a device of improved type for the separation of airborne particles into grain size classes characterised by the fact that it comprises:

a first base body on the upper face of which is formed a first cavity on the upper edge of which rests a plate on the upper surface of which is deposited a filter, the said plate having on its upper face a plurality of first annular grooves along each of which is formed a plurality of first through holes opening into the said first cavity in which, in use, there is created a depression;

a second hollow body fixed to the upper surface of the said first body and having a central portion describing with its inner surface the lateral surface of a frusto-conical solid with its portion of greater diameter positioned on the upper part of the said central portion;

a third body within the said second body and having a base wall facing the said plate and the lower surface of which defines with the upper surface of the said filter a second cavity, and a central portion of which extends upwardly from the lateral edge of the said base wall and describing with its outer surface the lateral surface of a frusto-conical solid the portion of greater diameter of which is positioned in the lower part in such a way as to define with the inner surface of the said central portion of the said second body a first annular channel of triangular section and communicating with the said second cavity by means of an outlet formed by suitably joining the lower ends of the said central portions respectively of the said second and third bodies, a quantity of filtered air being ducted along the said first channel towards the said second cavity; and an annular nozzle positioned in the said first channel and operable to eject into it, close to the said outlet, a quantity of particle-bearing air in such a way that the particles of dust present therein after having traversed the said outlet are deposited on the upper surface of the said filter.

BRIEF DESCRIPTION OF THE DRAWINGS

For a better understanding of the present invention a preferred embodiment thereof is now described, purely by way of non limitative example, with reference to the attached drawings, in which:

FIG. 1 is a partial section of a device for the separation of airborne particles into grain size classes; and FIG. 2 is a view on an enlarged scale of a detail of the device of FIG. 1.

DETAILED DESCRIPTION OF THE INVENTION

As illustrated in FIG. 1, a device of improved type for the separation of aerosol particles into grain size classes is generally indicated with the reference numeral 1. The device 1 has a cylindrical base body 2 on the upper surface of which is formed a cylindrical cavity 3. In correspondence with the cavity 3 on the body 2 there is formed a threaded through hole 4 into which is screwed an upper threaded portion 5 of a pipe union 6 a lower portion 7 of which projects out from the body 2 from the lower surface of this. In use, the pipe union 6 is in communication via a duct not illustrated with a pump able to create a depression in the cavity 3. On the upper edge of the cavity 3 there is formed an annular rebate 8 upon which rests the perimetral edge of a cylindrical plate 11 on which, with the interposition of a mesh 12 of circular outline (FIG. 2), there is deposited a filter 13 also of circular outline. On the upper surface of the plate 11 there are formed a plurality of concentric annular grooves 14. Along each groove 14 there is formed a plurality of through holes 15 the axes of which are orthogonal to the longitudinal axis of the groove 14. In use, the fluid composed of filtered air and aerosol, stripped of the particles which have been deposited on the filter, pass through this latter and enter the cavity 3 by passing through the groove 14 and the holes 15. The thickness of the assembly comprising the plate 11, mesh 12 and filter 13 is equal to the vertical depth of the recess 8 in such a way that the upper surface of the filter 13 is coplanar with the upper surface of the body 2. The filter 13 is preferably of the membrane type, that is to say formed with a porous material such as cellulose or teflon.

Figure 1:
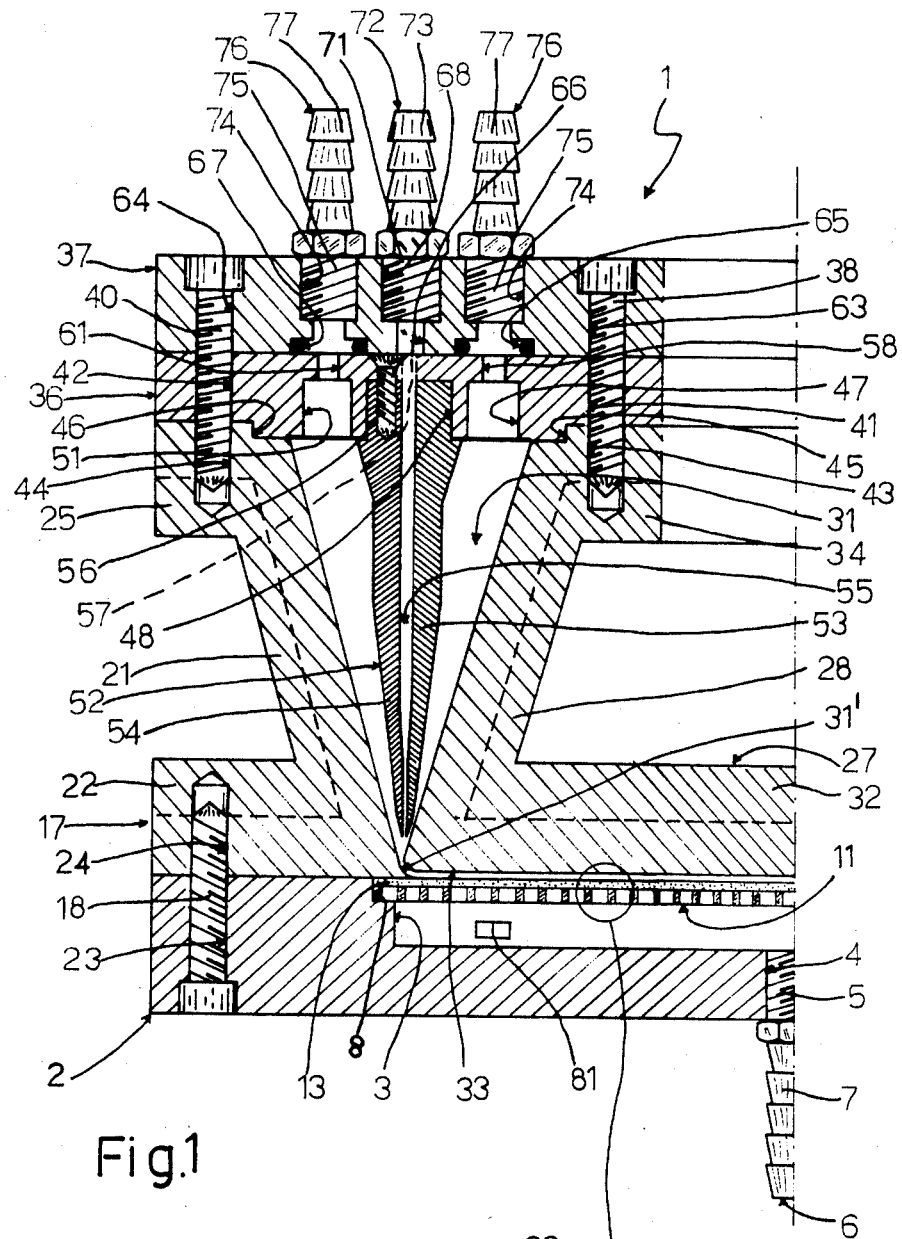

As illustrated in FIG. 1, the device 1 includes an annular body 17 coaxial with the body 2 and in fact fixed to this latter by screws 18. The body 17 has a middle portion 21 of substantially frusto-conical form and of constant thickness positioned with the larger diameter end uppermost. From the lower end of the portion 21 an annular projection 22 extends radially outwardly, this projection having its lower surface facing a peripheral region of the upper surface of the body 2. This latter has a plurality of through holes 23 coaxial with a corresponding number of blind threaded holes 24 formed in the projection 22. The screws 18 first engage the holes 23 and subsequently are screwed into the holes 24. From the upper end of the portion 21 a second annular projection 25 extends outwardly parallel to the projection 22.

The device 1 further includes an annular body 27 coaxial with the body 17 and rather inward of this latter. The body 27 has a central portion 28 of substantially frusto-conical form, of constant thickness, and having the lower end of greater diameter. The inner surface of the portion 21 of the body 17 and the outer surface of the portion 28 of the body 27 define an annular channel 31 having a width decreasing from the top towards the bottom. The lower end of the portion 28 joins to the perimetral edge of a cylindrical plate 32 having a thickness less than that of the projection 22, that is to say with its lower surface facing but at a predetermined distance from the upper surface of the filter 13 which as has already been indicated is coplanar with the upper surface of the body 2. Between the lower surface of the plate 32 and the upper surface of the filter 13 there is therefore defined a cylindrical cavity 33 of reduced depth. The assembly comprising the plate 11, mesh 12 and filter 13 is therefore a dividing wall between the cavities 3 and 33. It is to be noted that the cavity 33 is in communication with the channel 31 by the fact that the lower ends of the portions 21 and 28 lie at a predetermined if small distance from one another. As illustrated in the drawings, it is to be noted that the said ends do not have sharp corners since these are suitably rounded or bevelled. The space within the channel 31 defined by the said ends of the portions 21 and 28 will hereinafter be called the outlet and indicated 31'. From the upper end of the portion 28 an annular projection 34 extends inwardly coplanar with the projection 25.

The device 1 includes two annular plates 36 and 37 coaxial with one another and with the bodies 17 and 24. In particular the radially inner ring of the plates 36 and 37 are fixed by screws 38 to the projection 34 of the body 27 and their radially outer rims are fixed by screws 40 to the projection 25 of the body 17. The plate 36 rests directly on the upper surface of the projections 25 and 34 and in this connection has on the inner peripheral region a plurality of through holes 41 and on the outer peripheral region a plurality of through holes 42. The holes 41 are coaxial with corresponding threaded blind holes 43 formed in the projection 34 and the holes 42 are coaxial with corresponding threaded blind holes 44 formed in the projection 25. The central ring of the plate 36 has a greater thickness than the inner and outer rims. The inner and outer edges of this central ring rest respectively on an annular rebate 45 formed at the upper end of the portion 28 and on an annular rebate 46 formed at the upper end of the portion 21.

The lower surface of the central ring of the plate 36 faces the channel 31 and has three annular grooves 4 respectively indicated 47, 48 and 51. The grooves 47 and 51 are respectively the innermost and the outermost and have the same width. The groove 48, which is the central groove, has a greater width than the others and houses the upper end of a nozzle 52 constituted by two annular bodies 53 and 54 coaxial with one another and to the bodies 17 and 27. The bodies 53 and 54 are concentric and define between them an annular channel 55. The bodies 53 and 54, of which that indicated 53 is inside the other, are fixed to the plate 36 with their upper ends by means of a plurality of screws 56 of which, for simplicity, only one is illustrated in FIG. 1, and which fix the body 54 to the plate 36. Along the groove 48 in the plate 36 there is formed a plurality of through holes 57 one of which is indicated with broken outlines in FIG. 1. The holes 57 open below into the channel 55. Along the grooves 47 and 51 in the plate 36 there is formed a respective plurality of through holes 58 and 61 similar to the holes 57. The plate 37 rests on the plate 36 and has an inner ring of through holes 63 coaxial with the holes 41 and an outer ring of through holes 64 coaxial with the holes 42. Each screw 38 engages in succession the hole 63 and the hole 41 and is screwed into the hole 43. Each screw 40 engages in succession the hole 64 and the hole 42 and is screwed into the hole 44. The central ring of the plates 37 which is in correspondence with the central ring of the plate 36 has on its lower surface three annular grooves 65, 66 and 67 of which the groove 65 which is the innermost is formed in correspondence with the holes 58, the groove 56, which is the central one, is formed in correspondence with the holes 57, and the groove 67, which is the outermost, is formed in correspondence with the hole 61. Along the groove 66 on the plate 37 there are formed threaded holes 68 into which there is screwed the lower threaded part 71 of a respective pipe union 72 having an upper part 73 extending upwardly out from the hole 68. Along the grooves 65 and 67 are formed respective threaded holes 74 into which there is screwed the lower threaded part 75 of a respective pipe union 76 having an upper part 77 extending upwardly out from the respective hole 74. In use, the pipe unions 72 are connected by ducts not illustrated to a source of aerosol (particle-bearing air)

connected to a source of filtered air by respective ducts not illustrated.

The operation of the device 1 is as follows.

In detail, constant quantity of filtered air is injected into the channel 31 from a suitable source and a constant quantity of dust-bearing air or aerosol is ejected, via the nozzle 52, into the channel 31 in correspondence with the outlet 31' from a second source which could be the environment itself. This is possible, for example, by connecting the pipe union 6 and therefore the interior of the cavity 3 with a pump able to create a depression in the cavity 3 which draws in the filtered air and the aerosol. As is known, an aerosol is simply air in which there are present particles in suspension. The fluid constituted by the filtered air and the particle-bearing air is subsequently introduced into the cavity 33. Since to enter into the cavity 33 this fluid must pass a sharp curvature (outlet 31') the particles of dust present in the aerosol become separated upon passing the curve into various bands of fluid according to their aerodynamic diameter, and all of the particles of the same grain size class will be present in its own band of fluid. After having traversed the curvature the particles commence to deposit on the filter starting from the particles of greater diameter. The fluid stripped of the particles will first enter into the cavity 3 and subsequently flow out from the device 1 towards the said pump through the pipe union 6. On the filter 13 there is therefore obtained a deposit differentiated according to the grain size class to which the particles belong. In particular, on the portion of the filter 13 closest the outlet 31' the particles of greater diameter will be deposited. Subsequently it is possible to extract the filter 13 and effect on the deposited particles all the analyses which are considered necessary.

The technique first indicated for the separation into grain size classes of the particles of dust is known and is described in various scientific publications. It consists in the fact that the particles traversing a sharp curve (outlet 31') tend, by inertia, to maintain their velocity in the direction and sense but are drawn along by the flow of fluid. The particles therefore separate from the initial fluid strain leaving the nozzle 52 by a distance which is a function only of the aerodynamic diameter. According to the known technique a clearly defined separation between the particles of different diamter is not obtained, in particular between those of smaller diameter. With the device of the invention the separation between the particles of different diameter is on the other hand enlarged since recourse is had to a projection on a wall (filter 13) positioned downstream of the curvature. It is to be noted, finally, that for a correct operation of the device and, that is to say, to obtain a greater separation of the particles into the various grain size classes, the longitudinal axis of a representative section of the nozzle 52 (FIG. 1) is displaced towards the outer lateral wall of the portion 28. This characteristic has been experimentally validated and is described in the said publications.

With respect to devices currently in commercial use, which have a rectangular filter and therefore a cavity, corresponding to the cavity 33, of substantially prismatic form, the device 1 with the circular filter 13 permits an elongation of the zone of separation of the particles, the elimination of the side walls of the cavity 33, and a greater linearisation of the curve obtained in a diagram which plots in abscissae the distance of the deposition starting from the curvature (outlet 31') and along the ordinate the aerodynamic diameter of the particles. This indicates that with this particular geometry of the filter 13 the particles of smaller diameter, which are the last to be deposited on the filter 13, will become deposited on a central ring on the filter 13 which is wider than the peripheral ring on which the particles of greater diameter are deposited. Finally, by studying a band of particles of large diameter and a band of particles of small diameter it has been ascertained that the respective annular portions of the filter 13 on which the two bands have been deposited have the same area. But since the portion on which the particles of smaller diameter have been deposited is the innermost, it follows that this portion must have a greater width than the other. This permits greater information to be obtained about the deposition of the particles of smaller diameter and therefore, on the basis of this, to have a better linearisation of the part of the curve of the diagram relaring to such particles, which are those of greater interest for environmental health that is to say for testing the toxicity of a given environment.

The aerodynamic separation of the particles in fact permits the mass, activity, form, density and other characteristics of the particles themselves to be studied. The interposition of the mesh 12 between the filter 13 and the plate 11 permits the particles to be deposited on the whole of the filter 13, that is to say even in those portions of the filter 13 corresponding to the solid parts of the plate 11 between two contiguous grooves 14.

With reference to FIG. 1, by utilising the device 1 it is possible to apply the $\beta$ absorption technique for real time determination of the mass of particles deposited on the filter 13. To apply this technique it is sufficient to dispose in the cavity 3 a source 81 of $\beta$ radiation and in the cavity 33 a detector 82 (FIG. 2) for example of the surface barrier diode type. The $\beta$ radiations transverse the hole 15 and the associated groove 14.

From what has been explained above the advantages consequent on the production of the present invention will be apparent.

In particular, with the detailed geometry of the channel 31, nozzle 52 and cavity 33, and of the filter 13 an elongation of the particle deposition zone is obtained, especially for those of smaller diameter. That is to say, the information relating to the particles of smaller diameter is not lost as is the case in currently commercially available devices. This appears more evident from the fact that the parts of the curve of the diagram relating to these particles is more linear than that obtained with information derived from currently available devices. With the device 1 it is possible to apply the $\beta$ absorption technique.

Finally, it is clear that the device 1 described and illustrated here can be modified and varied without by this departing from the scope of the present invention.

I claim:

1. A device employing a source of filtered air and a source of negative pressure for the separation of airborne particles into grain size classes, comprising:

a base body having a first cylindrical cavity provided on the uppermost face thereof and adapted to be connected with said source of negative pressure, said base body having a plate resting on the upper edge of said first cavity, and a filter deposited flush with said uppermost face of said base body on an upper surface of said plate, the latter having a plurality of first through holes opening into said first cavity and at least a first annular groove formed on said upper surface of said plate along said through holes;

a hollow body fixed to the upper surface of said base body and having a central portion describing with its inner surface the lateral surface of a frusto-conical solid coaxial with said first cavity and having the region of greater diameter located in the upper part of said central portion;

a first body provided within said hollow body and having a base wall facing said plate and the lower surface of which defines, with the upper surface of said filter a second cylindrical cavity coaxial with said first cavity, and a central portion extending upwardly from the lateral edge of said base wall and describing with its outer surface the lateral surface of a frustro-conical body coaxial with said second cavity and having the portion of greater diameter located in the lower part in such a way as to define with the inner surface of said central portion of said hollow body an annular channel shaped to have a triangular section coaxial with said second cavity and positioned to communicate with the periphery of the same via a 90° degree bend defined by the lower ends of said central portions, respectively, of said hollow and first bodies, said annular channel and means for connecting to said source of filtered air; and an annular nozzle positioned in said first channel and operable to eject, close to said 90° degree bend a quantity of particle-bearing air in such a way that particles of dust present therein after having traversed said bend flow through said second cavity from the periphery towards its center and are deposited on the upper surface of said filter.

2. A device according to claim 1, characterized by the fact that the said filter has a circular outline.

3. A device according to claim 2 characterized by the fact that between the said filter and the said plate there is interposed a mesh of circular outline.

4. A device according to claim 2 characterized by the fact that in the said first cavity there is formed a second through hole engaged by a first pipe union connectable to a pump operable to create a partial vacuum within the said first cavity.

5. A device according to claim 1, characterized by the fact that said annular nozzle includes two annular elements defining between them a second annular channel communicating with a source of particle bearing air.

6. A device according to claim 5, characterized by the fact that the said nozzle is disposed in said annular channel in such a way as to be closer to the said central portion of the said first body.

7. A device according to claim 5, wherein said annular elements are supported by a first plate positioned about said hollow and first bodies and fixed to these by a plurality of screws in such a way that said hollow body supports said first body by means of said first plate.

8. A device according to claim 7, characterized by the fact that it includes a second plate positioned above said first plate and in which there is formed a third hole which can be engaged by a second pipe union connected to the source of particle-bearing air; said third hole communicating, via a plurality of fourth holes formed in said first plate with said second channel.

9. A device according to claim 8, characterized by the fact that in the said second plate there is formed at least a fifth hole which can be engaged by a third pipe union connected to the source of filtered air; the said fifth communicating, via a plurality of sixth holes formed in the said first plate, with the said first channel.

10. A device according to claim 9, characterized by the fact that the said first plate has its lower surface facing the said annular channel a second annular groove in which there are fixed the upper ends of the said annular elements along the said second groove there being formed the said fourth holes communicating below with the said second channel and above by means of a third annular groove formed on the said lower surface of the said second plate with the said third hole formed in the said third groove.

11. A device according to claim 9, characterized by the fact that the said first plate has on its lower surface facing the said first channel at least a fourth annular groove concentric with the said second groove and open towards the said first channel within the said fourth groove there being formed the said sixth holes communicating above, via a fifth annular groove formed on the lower surface of the said second plate concentrically with the said third groove, with the said fifth holes formed in the said fifth groove.

12. A device according to claim 1 wherein within said first cavity there is positioned a source of $\beta$ radiation; there being deposited on the surface of said second cavity a detector.

13. A device according to claim 12, wherein said detector is of the surface barrier type.

* * * * *